US010010313B2

(12) United States Patent
Arden et al.

(10) Patent No.: US 10,010,313 B2
(45) Date of Patent: Jul. 3, 2018

(54) MANDIBULAR SUBLUXATION DEVICE AND METHOD

(71) Applicant: Richard L. Arden, Farmington Hills, MI (US)

(72) Inventors: Richard L. Arden, Farmington Hills, MI (US); John F. Goodman, Ann Arbor, MI (US)

(73) Assignee: Richard L. Arden, Farmington Hills, MI (US)

( * ) Notice: Subject to any disclaimer, the term of this patent is extended or adjusted under 35 U.S.C. 154(b) by 266 days.

(21) Appl. No.: 15/158,224

(22) Filed: May 18, 2016

(65) Prior Publication Data

US 2016/0338684 A1 Nov. 24, 2016

Related U.S. Application Data

(60) Provisional application No. 62/163,007, filed on May 18, 2015.

(51) Int. Cl.
*A61B 17/02* (2006.01)
*A61B 1/24* (2006.01)
(Continued)

(52) U.S. Cl.
CPC ............ *A61B 17/025* (2013.01); *A61B 17/24* (2013.01); *A61B 90/16* (2016.02); *A61B 2017/00407* (2013.01)

(58) Field of Classification Search
CPC ....... A61B 17/025; A61B 90/16; A61B 17/24; A61B 2017/00407
See application file for complete search history.

(56) References Cited

U.S. PATENT DOCUMENTS 900,541 A 10/1908 Holmes
2,127,215 A 8/1938 Gwathmey
(Continued)

FOREIGN PATENT DOCUMENTS

CN 205251810 4/2016
DE 10216242 4/2003
(Continued)

OTHER PUBLICATIONS

Snore RX Review, [Mouthpiece For Snoring Reviews], unknown publication date; http://mouthpieceforsnoringreviews.com/snorerx-review/ accessed Apr. 25, 2015.

*Primary Examiner* — Christian Sevilla
(74) *Attorney, Agent, or Firm* — Reising Ethington P.C.

(57) ABSTRACT

A mandibular subluxation device (MSD) is provided. The device includes an upper MSD component and a lower MSD component. The upper MSD component includes and upper tooth guide connected to an upper plate having a pair of depending legs. The upper MSD component further includes an upper force receiving plate. The MSD also includes a lower MSD component. The lower MSD component includes a lower tooth guide connected to a lower plate. The lower MSD component further includes a lower force receiving plate. The upper and lower MSD components are connected in a way that allows relative longitudinal movement between the two components between a neutral position and a plurality of extended positions. A ratchet mechanism inhibits movement of the lower plate from any extended position toward the neutral position. The ratchet mechanism may be manually disengaged to allow the lower MSD component to return to the neutral position.

13 Claims, 8 Drawing Sheets

(51) Int. Cl.
  *A61B 17/24* (2006.01)
  *A61B 17/00* (2006.01)
  *A61B 90/16* (2016.01)

(56) References Cited

U.S. PATENT DOCUMENTS

| | | |
|---|---|---|
| 2,521,084 A | 9/1950 | Oberto |
| 2,669,988 A | 2/1954 | Carpenter |
| 2,823,455 A | 2/1958 | Sprague |
| 2,882,893 A | 4/1959 | Godfroy |
| 3,132,647 A | 5/1964 | Giuseppe |
| 3,321,832 A | 5/1967 | Weisberg |
| 3,353,271 A | 11/1967 | Blechman |
| 3,461,858 A | 8/1969 | Michelson |
| 4,112,936 A | 9/1978 | Blachly |
| 4,169,473 A | 10/1979 | Samelson |
| 4,226,234 A | 10/1980 | Gunderson |
| 4,270,531 A | 6/1981 | Blachly |
| 4,304,227 A | 12/1981 | Samelson |
| 4,382,783 A | 5/1983 | Rosenberg |
| 4,425,911 A | 1/1984 | Luomanen |
| 4,439,147 A | 3/1984 | Keys |
| 4,495,945 A | 1/1985 | Liegner |
| 4,505,672 A | 3/1985 | Kurz |
| 4,715,368 A | 12/1987 | George |
| 4,806,100 A | 2/1989 | Schainholz |
| 4,821,715 A | 4/1989 | Downing |
| 4,862,903 A | 9/1989 | Avenue |
| 4,901,737 A | 2/1990 | Toone |
| 4,928,710 A | 5/1990 | Avenue |
| 4,955,367 A | 9/1990 | Homsy |
| 4,969,822 A | 11/1990 | Summer |
| 4,978,323 A | 12/1990 | Freedman |
| 5,003,994 A | 4/1991 | Cook |
| 5,031,611 A | 7/1991 | Moles |
| 5,050,586 A | 9/1991 | Bonnell |
| 5,062,422 A | 11/1991 | Donarudo |
| 5,066,226 A | 11/1991 | Summer |
| 5,082,007 A | 1/1992 | Adell |
| 5,092,346 A | 3/1992 | Meade |
| 5,117,816 A | 6/1992 | Shapiro |
| 5,154,609 A | 10/1992 | George |
| 5,176,594 A | 1/1993 | Lee |
| 5,176,618 A | 1/1993 | Freedman |
| 5,203,324 A | 4/1993 | Donarudo |
| 5,273,032 A | 12/1993 | Borody |
| 5,277,202 A | 1/1994 | Hays |
| 5,305,741 A | 4/1994 | Moles |
| 5,313,960 A | 5/1994 | Tomasi |
| D348,932 S | 7/1994 | Jackson |
| 5,365,945 A | 11/1994 | Halstrom |
| 5,409,017 A | 4/1995 | Lowe |
| 5,413,095 A | 5/1995 | Weaver |
| 5,427,117 A | 6/1995 | Thornton |
| 5,462,066 A | 10/1995 | Snyder |
| 5,466,153 A | 11/1995 | Poindexter |
| 5,467,783 A | 11/1995 | Meade |
| 5,494,048 A | 2/1996 | Carden |
| 5,499,633 A | 3/1996 | Fenton |
| 5,513,634 A | 5/1996 | Jackson |
| 5,513,986 A | 5/1996 | Feltham |
| 5,524,639 A | 6/1996 | Lanier |
| 5,537,994 A | 7/1996 | Thornton |
| 5,566,683 A | 10/1996 | Thornton |
| 5,570,704 A | 11/1996 | Agre |
| 5,590,643 A | 1/1997 | Flam |
| 5,632,283 A | 5/1997 | Carden |
| 5,638,811 A | 6/1997 | David |
| 5,642,737 A | 7/1997 | Parks |
| 5,660,174 A | 8/1997 | Jacobelli |
| 5,682,632 A | 11/1997 | Cotroneo |
| 5,682,903 A | 11/1997 | Meade |
| 5,683,244 A | 11/1997 | Truax |
| 5,720,302 A | 2/1998 | Belfer |
| 5,752,510 A | 5/1998 | Goldstein |
| 5,752,822 A | 5/1998 | Robson |
| 5,755,219 A | 5/1998 | Thornton |
| 5,779,470 A | 7/1998 | Kussick |
| 5,794,627 A | 8/1998 | Frantz |
| 5,806,516 A | 9/1998 | Beattie |
| 5,810,013 A | 9/1998 | Belfer |
| 5,816,799 A | 10/1998 | Parker |
| 5,823,193 A | 10/1998 | Gottehrer |
| 5,829,441 A | 11/1998 | Kidd |
| 5,846,212 A | 12/1998 | Beeuwkes, III |
| 5,868,138 A | 2/1999 | Halstrom |
| 5,876,199 A | 3/1999 | Bergersen |
| 5,884,625 A | 3/1999 | Hart |
| 5,884,628 A | 3/1999 | Hilsen |
| 5,893,365 A | 4/1999 | Anderson |
| 5,921,241 A | 7/1999 | Belfer |
| 5,941,246 A | 8/1999 | Roopchand |
| 5,941,247 A | 8/1999 | Keane |
| 5,947,724 A | 9/1999 | Frantz |
| 5,950,624 A | 9/1999 | Hart |
| 5,954,048 A | 9/1999 | Thornton |
| 5,957,133 A | 9/1999 | Hart |
| 5,967,784 A | 10/1999 | Powers |
| 5,979,456 A | 11/1999 | Magovern |
| 5,983,892 A | 11/1999 | Thornton |
| 5,988,170 A | 11/1999 | Thomas |
| 6,041,784 A | 3/2000 | Halstrom |
| 6,055,986 A | 5/2000 | Meade |
| 6,109,265 A | 8/2000 | Frantz |
| 6,129,084 A | 10/2000 | Bergersen |
| 6,161,542 A | 12/2000 | Halstrom |
| 6,168,601 B1 | 1/2001 | Martini |
| 6,170,485 B1 | 1/2001 | Orrico |
| 6,171,314 B1 | 1/2001 | Rotramel |
| 6,200,285 B1 | 3/2001 | Towliat |
| 6,209,542 B1 | 4/2001 | Thornton |
| 6,244,865 B1 | 6/2001 | Salemi |
| 6,257,238 B1 | 7/2001 | Meah |
| 6,305,376 B1 | 10/2001 | Thornton |
| 6,325,064 B1 | 12/2001 | Thornton |
| 6,371,112 B1 | 4/2002 | Bibi |
| 6,374,824 B1 | 4/2002 | Thornton |
| 6,394,093 B1 | 5/2002 | Lethi |
| 6,405,729 B1 | 6/2002 | Thornton |
| 6,418,933 B1 | 7/2002 | Strong |
| 6,450,167 B1 | 9/2002 | David |
| 6,464,924 B1 | 10/2002 | Thornton |
| 6,505,625 B1 | 1/2003 | Uenishi |
| 6,505,626 B2 | 1/2003 | Belvedere |
| 6,505,627 B2 | 1/2003 | Belvedere |
| 6,505,628 B2 | 1/2003 | Belvedere |
| 6,508,251 B2 | 1/2003 | Belvedere |
| 6,510,853 B1 | 1/2003 | Belvedere |
| 6,516,805 B1 | 2/2003 | Thornton |
| 6,526,982 B1 | 3/2003 | Strong |
| 6,533,761 B2 | 3/2003 | Shepherd |
| 6,558,392 B1 | 5/2003 | Martini |
| 6,571,798 B1 | 6/2003 | Thornton |
| 6,584,975 B1 | 7/2003 | Taylor |
| 6,588,430 B2 | 7/2003 | Belvedere |
| 6,604,527 B1 | 8/2003 | Palmisano |
| 6,615,834 B2 | 9/2003 | Cresswell |
| 6,619,290 B1 | 9/2003 | Zacco |
| 6,626,169 B2 | 9/2003 | Gaitini |
| 6,637,436 B2 | 10/2003 | Farrell |
| 6,662,803 B2 | 12/2003 | Cresswell |
| 6,675,802 B1 | 1/2004 | Thornton |
| 6,675,806 B2 | 1/2004 | Belvedere |
| 6,675,808 B2 | 1/2004 | Karasic |
| 6,679,257 B1 | 1/2004 | Gradon |
| 6,691,710 B2 | 2/2004 | Belvedere |
| 6,701,926 B2 | 3/2004 | Cresswell |
| 6,729,335 B1 | 5/2004 | Halstrom |
| 6,769,910 B1 | 8/2004 | Pantino |
| 6,789,541 B2 | 9/2004 | Cresswell |
| 6,789,543 B2 | 9/2004 | Cannon |
| 6,805,127 B1 | 10/2004 | Karasic |
| 6,820,617 B2 | 11/2004 | Gradon |
| 6,832,610 B2 | 12/2004 | Cresswell |

(56) References Cited

U.S. PATENT DOCUMENTS

| | | |
|---|---|---|
| 6,845,774 B2 | 1/2005 | Gaskell |
| 6,860,270 B2 | 3/2005 | Sniadach |
| 6,877,513 B2 | 4/2005 | Barnett |
| 6,890,322 B2 | 5/2005 | Shepherd |
| 6,895,970 B1 | 5/2005 | Berghash |
| 6,926,007 B2 | 8/2005 | Frank |
| 6,932,598 B1 | 8/2005 | Anderson |
| 6,935,857 B1 | 8/2005 | Farrell |
| 6,951,218 B2 | 10/2005 | Cresswell |
| 6,969,366 B1 | 11/2005 | Reddick |
| 6,981,502 B2 | 1/2006 | Anthony |
| 6,988,888 B2 | 1/2006 | Cleary |
| 6,997,186 B2 | 2/2006 | Gradon |
| 7,001,180 B2 | 2/2006 | Bass |
| 7,004,172 B1 | 2/2006 | Zacco |
| 7,017,576 B2 | 3/2006 | Cresswell |
| 7,021,312 B2 | 4/2006 | Toussaint |
| 7,032,597 B1 | 4/2006 | Frank |
| 7,047,976 B2 | 5/2006 | Frank |
| 7,047,977 B2 | 5/2006 | Frank |
| 7,055,524 B1 | 6/2006 | Taimoorazy |
| 7,077,138 B2 | 7/2006 | Bateman |
| 7,077,646 B2 | 7/2006 | Hilliard |
| 7,080,648 B2 | 7/2006 | Frank |
| 7,124,756 B1 | 10/2006 | Frank |
| 7,124,757 B2 | 10/2006 | Frank |
| 7,128,071 B2 | 10/2006 | Brain |
| 7,134,436 B2 | 12/2006 | Frank |
| 7,143,767 B2 | 12/2006 | Zacco |
| 7,146,982 B2 | 12/2006 | Baratier |
| 7,174,895 B2 | 2/2007 | Thornton |
| 7,178,529 B2 | 2/2007 | Kownacki |
| 7,243,649 B2 | 7/2007 | Irlbeck |
| 7,263,998 B2 | 9/2007 | Miller |
| 7,278,420 B2 | 10/2007 | Armstead |
| 7,299,804 B2 | 11/2007 | Belvedere |
| 7,311,103 B2 | 12/2007 | Jeppesen |
| 7,328,698 B2 | 2/2008 | Barnett |
| 7,328,705 B2 | 2/2008 | Abramson |
| 7,331,349 B2 | 2/2008 | Neville |
| 7,336,065 B1 | 2/2008 | Zacco |
| 7,364,429 B2 | 4/2008 | Olivier |
| 7,399,182 B2 | 4/2008 | Olivier |
| 7,404,402 B2 | 7/2008 | Farrell |
| 7,448,388 B2 | 11/2008 | Diacopoulos |
| 7,500,480 B2 | 3/2009 | Andrews |
| 7,520,281 B1 | 4/2009 | Nahabedian |
| 7,581,542 B2 | 9/2009 | Abramson |
| 7,597,103 B2 | 10/2009 | Thornton |
| 7,607,439 B2 | 10/2009 | Hedge |
| 7,624,736 B2 | 12/2009 | Borody |
| 7,637,262 B2 | 12/2009 | Bailey |
| 7,650,885 B2 | 1/2010 | Paoluccio |
| D615,187 S | 5/2010 | Bowden |
| 7,712,468 B2 | 5/2010 | Hargadon |
| 7,721,741 B2 | 5/2010 | Thornton |
| 7,730,890 B2 | 6/2010 | Enoch |
| 7,730,891 B2 | 6/2010 | Lamberg |
| 7,748,386 B2 | 7/2010 | Thornton |
| 7,757,693 B2 | 7/2010 | Toussaint |
| 7,762,263 B2 | 7/2010 | Rose |
| 7,766,016 B2 | 8/2010 | Rosenblum |
| 7,793,661 B2 | 9/2010 | Macken |
| 7,810,502 B1 | 10/2010 | Nguyen |
| 7,810,503 B2 | 10/2010 | Magnin |
| 7,819,122 B2 | 10/2010 | Abramson |
| 7,823,590 B2 | 11/2010 | Bibi |
| 7,832,402 B2 | 11/2010 | Nelissen |
| 7,832,403 B2 | 11/2010 | Diacopoulos |
| 7,836,888 B2 | 11/2010 | Bhat |
| 7,836,889 B2 | 11/2010 | Kusukawa |
| 7,841,346 B2 | 11/2010 | Yan |
| 7,866,313 B2 | 1/2011 | Hoy |
| 7,866,314 B2 | 1/2011 | Hoy |
| 7,870,860 B2 | 1/2011 | Anthony |
| D631,969 S | 2/2011 | King |
| 7,882,842 B2 | 2/2011 | Bhat |
| D634,015 S | 3/2011 | King |
| 7,896,003 B2 | 3/2011 | Andrews |
| 7,896,007 B2 | 3/2011 | Brain |
| 7,905,232 B2 | 3/2011 | Cresswell |
| 7,935,065 B2 | 5/2011 | Bihari |
| 7,946,288 B2 | 5/2011 | Flynn |
| 7,951,102 B2 | 5/2011 | Gefen |
| 7,954,494 B1 | 6/2011 | Connor |
| 7,963,286 B2 | 6/2011 | Burdumy |
| 7,975,689 B2 | 7/2011 | Hauge |
| 7,980,248 B2 | 7/2011 | Bhat |
| 8,001,970 B2 | 8/2011 | Young |
| 8,001,973 B2 | 8/2011 | Branscum, Jr. |
| 8,025,063 B2 | 9/2011 | Branscum, Jr. |
| 8,028,704 B2 | 10/2011 | Reynolds, II |
| 8,028,705 B2 | 10/2011 | Hedge |
| 8,037,886 B2 | 10/2011 | Branscum, Jr. |
| 8,042,547 B2 | 10/2011 | Goldstein |
| 8,074,656 B2 | 12/2011 | Crowe |
| 8,082,923 B2 | 12/2011 | Doctors |
| 8,091,554 B2 | 1/2012 | Jiang |
| 8,100,126 B2 | 1/2012 | Cresswell |
| 8,104,467 B2 | 1/2012 | Napier |
| 8,109,271 B2 | 2/2012 | Vandine |
| 8,122,889 B2 | 2/2012 | Crowe |
| 8,122,890 B2 | 2/2012 | Crowe |
| 8,123,521 B1 | 2/2012 | Kopp |
| 8,127,769 B2 | 3/2012 | Kimani |
| 8,136,529 B2 | 3/2012 | Kelly |
| 8,156,940 B2 | 4/2012 | Lee |
| 8,166,976 B2 | 5/2012 | Lieberman |
| 8,191,553 B2 | 6/2012 | Stone |
| 8,205,617 B2 | 6/2012 | Stygar |
| 8,215,312 B2 | 7/2012 | Garabadian |
| 8,220,461 B1 | 7/2012 | Guerra |
| 8,226,407 B2 | 7/2012 | Hanewinkel, III |
| 8,251,069 B2 | 8/2012 | Burdumy |
| 8,256,426 B2 | 9/2012 | Abramson |
| 8,262,596 B2 | 9/2012 | Gefen |
| 8,297,275 B2 | 10/2012 | Ogilvie |
| 8,316,857 B2 | 11/2012 | Thornton |
| 8,316,858 B2 | 11/2012 | Thornton |
| 8,321,884 B2 | 11/2012 | Fuselier |
| 8,336,550 B2 | 12/2012 | Goldstein |
| 8,336,553 B2 | 12/2012 | Bhat |
| 8,347,890 B2 | 1/2013 | Hedge |
| 8,356,592 B2 | 1/2013 | Andrews |
| 8,356,603 B2 | 1/2013 | Thornton |
| 8,372,020 B2 | 2/2013 | Bihari |
| 8,413,658 B2 | 4/2013 | Williams |
| 8,443,797 B2 | 5/2013 | Hauge |
| 8,474,458 B1 | 7/2013 | Yadven |
| 8,485,194 B2 | 7/2013 | Guerra |
| 8,505,540 B2 | 8/2013 | Crowe |
| 8,517,029 B2 | 8/2013 | Nelissen |
| 8,534,278 B2 | 9/2013 | Colman |
| 8,544,472 B2 | 10/2013 | Gaskell |
| 8,550,816 B2 | 10/2013 | Hanewinkel, III |
| 8,555,886 B2 * | 10/2013 | Colman ............ A61B 1/00154 128/200.26 |
| 8,573,223 B2 | 11/2013 | Crowe |
| 8,573,224 B2 | 11/2013 | Thornton |
| 8,578,937 B2 | 11/2013 | Bhat |
| 8,602,029 B2 | 12/2013 | Cresswell |
| 8,607,796 B2 | 12/2013 | Thornton |
| 8,613,279 B2 | 12/2013 | Cresswell |
| 8,613,283 B2 | 12/2013 | Hedge |
| 8,631,800 B2 | 1/2014 | Clark |
| 8,640,692 B2 | 2/2014 | Matioc |
| 8,646,455 B2 | 2/2014 | Lieberman |
| 8,656,922 B2 | 2/2014 | Vaska et al. |
| 8,656,925 B2 | 2/2014 | Davis |
| 8,656,926 B2 | 2/2014 | Doctors |
| 8,662,084 B2 | 3/2014 | Thornton |
| 8,667,970 B2 | 3/2014 | Podmore et al. |
| 8,671,946 B2 | 3/2014 | Thornton |
| 8,684,006 B2 | 4/2014 | Morgan |

(56) References Cited

U.S. PATENT DOCUMENTS

| | | |
|---|---|---|
| 8,684,007 B2 | 4/2014 | Timmons |
| 8,684,919 B2 | 4/2014 | Anca |
| 8,701,672 B2 | 4/2014 | Crowe |
| 8,714,157 B2 | 5/2014 | Cresswell |
| 8,739,794 B2 | 6/2014 | Cutler |
| 8,757,164 B2 | 6/2014 | Abramson |
| 8,770,189 B2 | 7/2014 | Colman |
| 8,783,259 B2 | 7/2014 | Spencer |
| 8,783,260 B2 | 7/2014 | Hugo |
| 8,783,261 B2 | 7/2014 | Thornton |
| 8,783,263 B2 | 7/2014 | Baldwin |
| 8,783,280 B2 | 7/2014 | Remmers et al. |
| 8,813,753 B2 | 8/2014 | Bhat |
| 8,820,320 B2 | 9/2014 | Filipi |
| 8,833,374 B2 | 9/2014 | Fallon |
| 8,839,793 B2 | 9/2014 | Diaz |
| 8,857,439 B2 | 10/2014 | Hedge |
| 8,875,713 B2 | 11/2014 | Metz |
| 8,881,733 B1 | 11/2014 | Harkins |
| 8,893,719 B2 | 11/2014 | David |
| 8,910,626 B2 | 12/2014 | Andrews |
| 8,931,477 B2 | 1/2015 | Ogilvie |
| 8,931,486 B2 | 1/2015 | Halstrom |
| 8,931,488 B2 | 1/2015 | Evans |
| 8,936,466 B2 * | 1/2015 | Moffson ............ A61C 1/084 433/131 |
| 8,950,027 B2 | 2/2015 | Kitahara |
| 8,973,573 B2 | 3/2015 | Filipi |
| 9,050,198 B2 | 6/2015 | Kallen |
| 9,060,680 B2 | 6/2015 | Colman |
| 9,072,612 B2 | 7/2015 | Sethi |
| 9,095,454 B2 | 8/2015 | Bernard |
| 9,119,928 B2 | 9/2015 | Hauge |
| 9,132,254 B2 | 9/2015 | Anca |
| 9,138,169 B2 | 9/2015 | Beard |
| 9,144,512 B2 | 9/2015 | Wagner |
| 9,144,655 B2 | 9/2015 | Cresswell |
| 9,155,855 B2 | 10/2015 | Haycock |
| 9,173,765 B2 | 11/2015 | Stone |
| 9,186,473 B2 | 11/2015 | Colman |
| 9,192,454 B2 | 11/2015 | Klein |
| 9,204,991 B1 | 12/2015 | Harkins |
| 9,220,629 B2 | 12/2015 | Koike |
| 9,220,653 B2 | 12/2015 | Israel |
| 9,237,940 B2 | 1/2016 | Koeklue |
| 9,241,825 B2 | 1/2016 | Crowe |
| 9,265,681 B1 | 2/2016 | Bell |
| D752,760 S | 3/2016 | Raad |
| 9,333,413 B2 | 5/2016 | Evans |
| 9,339,410 B2 | 5/2016 | Smith |
| 9,339,621 B2 | 5/2016 | Cresswell |
| D760,889 S | 7/2016 | Evans |
| 9,408,743 B1 | 8/2016 | Wagner |
| 9,414,896 B2 | 8/2016 | Giffey |
| 9,439,802 B2 | 9/2016 | Wagner |
| 9,445,938 B1 | 9/2016 | Wagner |
| 9,545,330 B2 | 1/2017 | Bernard |
| 9,545,331 B2 | 1/2017 | Ingemarsson |
| 9,545,332 B2 | 1/2017 | Luco |
| 9,575,739 B2 | 2/2017 | Bell |
| 9,585,785 B2 | 3/2017 | Hofmann |
| 9,610,189 B2 | 4/2017 | Heinonena |
| 9,610,190 B2 | 4/2017 | Crowe |
| 9,615,964 B2 | 4/2017 | Rogers |
| 9,629,975 B1 | 4/2017 | Kane |
| 9,655,692 B2 | 5/2017 | Lucas |
| 9,655,766 B2 | 5/2017 | Wood |
| 9,655,768 B2 | 5/2017 | Crowe |
| 9,669,174 B2 | 6/2017 | Hoy |
| 9,687,623 B2 | 6/2017 | Colman |
| 9,655,695 B2 | 7/2017 | Ross |
| 9,707,121 B2 | 7/2017 | Wood |
| 9,707,368 B2 | 7/2017 | Cresswell |
| 9,717,975 B2 | 8/2017 | Evans |
| 9,744,006 B2 | 8/2017 | Ross |
| 9,744,070 B2 | 8/2017 | Chung |
| 9,802,021 B2 | 10/2017 | Haycock |
| 9,820,881 B2 | 11/2017 | Aarestad |
| 9,820,882 B2 | 11/2017 | David |
| D805,644 S | 12/2017 | Lesser |
| 9,844,424 B2 | 12/2017 | Ali |
| 9,849,259 B2 | 12/2017 | Colman |
| 9,867,753 B2 | 1/2018 | Garay |
| 9,867,957 B2 | 1/2018 | Colman |
| 2002/0069872 A1 | 6/2002 | Alan Smith |
| 2003/0015198 A1 | 1/2003 | Britt |
| 2005/0028826 A1 | 2/2005 | Palmisano |
| 2005/0051178 A1 | 3/2005 | Sawford |
| 2005/0175954 A1 | 8/2005 | Zacher |
| 2005/0274386 A1 | 12/2005 | Macken |
| 2005/0274387 A1 | 12/2005 | Macken |
| 2006/0174897 A1 | 8/2006 | Sarkisian |
| 2006/0201520 A1 | 9/2006 | Christensen, III |
| 2006/0207597 A1 | 9/2006 | Wright |
| 2007/0006878 A1 | 1/2007 | Mackey |
| 2007/0068534 A1 | 3/2007 | Bailey |
| 2007/0079833 A1 | 4/2007 | Lamberg |
| 2007/0089752 A1 | 4/2007 | Christensen |
| 2007/0113844 A1 | 5/2007 | Garren |
| 2007/0135770 A1 | 6/2007 | Cropper |
| 2007/0287598 A1 | 12/2007 | Christensen, III |
| 2008/0053434 A1 | 3/2008 | Atkinson |
| 2008/0072915 A1 | 3/2008 | Nelissen |
| 2008/0115791 A1 | 5/2008 | Heine |
| 2008/0149110 A1 | 6/2008 | Baldwin |
| 2008/0149114 A1 | 6/2008 | Baldwin |
| 2008/0153056 A1 | 6/2008 | Baldwin |
| 2008/0153057 A1 | 6/2008 | Baldwin |
| 2008/0156324 A1 | 7/2008 | Hoy |
| 2008/0173313 A1 | 7/2008 | Neville |
| 2008/0190437 A1 | 8/2008 | Hervy |
| 2008/0257358 A1 | 10/2008 | Alessandrini |
| 2009/0032030 A1 | 2/2009 | Callender |
| 2009/0036889 A1 | 2/2009 | Callender |
| 2009/0095309 A1 | 4/2009 | Derrick et al. |
| 2009/0098508 A1 | 4/2009 | Baldwin |
| 2009/0145442 A1 | 6/2009 | Hecox |
| 2009/0163838 A1 | 6/2009 | Hecox |
| 2009/0177124 A1 | 7/2009 | Oronsky |
| 2010/0030027 A1 | 2/2010 | Bastid |
| 2010/0065066 A1 | 3/2010 | Hamburg |
| 2010/0185059 A1 * | 7/2010 | Sperling ............ A61B 17/02 600/219 |
| 2010/0224198 A1 | 9/2010 | Ayuse |
| 2010/0261133 A1 | 10/2010 | Lax |
| 2010/0262033 A1 | 10/2010 | Colman |
| 2010/0307511 A1 | 12/2010 | Meade |
| 2011/0168188 A1 | 7/2011 | Moore |
| 2011/0195376 A1 | 8/2011 | Boyd |
| 2011/0253150 A1 | 10/2011 | Young |
| 2012/0041440 A1 | 2/2012 | Waddell |
| 2012/0204865 A1 | 8/2012 | Filipi |
| 2013/0098373 A1 | 4/2013 | Carlone |
| 2013/0112210 A1 | 5/2013 | Stein |
| 2013/0118507 A1 | 5/2013 | Chappuis |
| 2013/0263865 A1 | 10/2013 | Khast |
| 2014/0007868 A1 | 1/2014 | Eaton |
| 2014/0048078 A1 | 2/2014 | Aahnblad |
| 2014/0076332 A1 | 3/2014 | Luco |
| 2014/0130809 A1 | 5/2014 | Clark |
| 2014/0144450 A1 | 5/2014 | Aarestad |
| 2014/0216469 A1 | 8/2014 | Keropian |
| 2014/0275784 A1 | 9/2014 | Joyce |
| 2014/0349243 A1 | 11/2014 | Metz |
| 2014/0352700 A1 | 12/2014 | Ingemarsson |
| 2015/0007830 A1 | 1/2015 | Bruehlmann |
| 2015/0020812 A1 | 1/2015 | Keropian |
| 2015/0164682 A1 | 6/2015 | Grosse |
| 2015/0164726 A1 | 6/2015 | Plott |
| 2015/0182374 A1 | 7/2015 | Stenberg |
| 2015/0190599 A1 | 7/2015 | Colman |
| 2015/0238280 A1 | 8/2015 | Ali |
| 2015/0245940 A1 | 9/2015 | Hardcastle |
| 2016/0022429 A1 | 1/2016 | Colman |

(56) References Cited

U.S. PATENT DOCUMENTS

| | | |
|---|---|---|
| 2016/0058275 A1 | 3/2016 | Hu |
| 2016/0101008 A1 | 4/2016 | Stone |
| 2016/0120619 A1 | 5/2016 | Bons |
| 2016/0184127 A1 | 6/2016 | Kitahara |
| 2016/0287429 A1 | 10/2016 | Lin |
| 2016/0287831 A1 | 10/2016 | Haycock |
| 2016/0361192 A1 | 12/2016 | Gerschman |
| 2016/0367394 A1 | 12/2016 | Wagner |
| 2017/0000586 A1 | 1/2017 | Lesser |
| 2017/0000643 A1 | 1/2017 | Gelb |
| 2017/0007795 A1 | 1/2017 | Cataldo |
| 2017/0049607 A1 | 2/2017 | Auley |
| 2017/0087003 A1 | 3/2017 | Luco |
| 2017/0128256 A1 | 5/2017 | Metz |
| 2017/0143537 A1 | 5/2017 | Kuhns |
| 2017/0202644 A1 | 7/2017 | Ross |
| 2017/0209238 A9 | 7/2017 | Ali |
| 2017/0231723 A1 | 8/2017 | Lucas |
| 2017/0266402 A1 | 9/2017 | Hoy |

FOREIGN PATENT DOCUMENTS

| | | |
|---|---|---|
| EP | 3209241 | 8/2017 |
| FR | 2820307 | 8/2004 |
| JP | 4115012 | 7/2008 |
| KR | 101479025 | 1/2015 |
| WO | 07014429 | 2/2007 |
| WO | 15127443 | 8/2015 |
| WO | 17149523 | 9/2017 |
| WO | 17152030 | 9/2017 |

\* cited by examiner

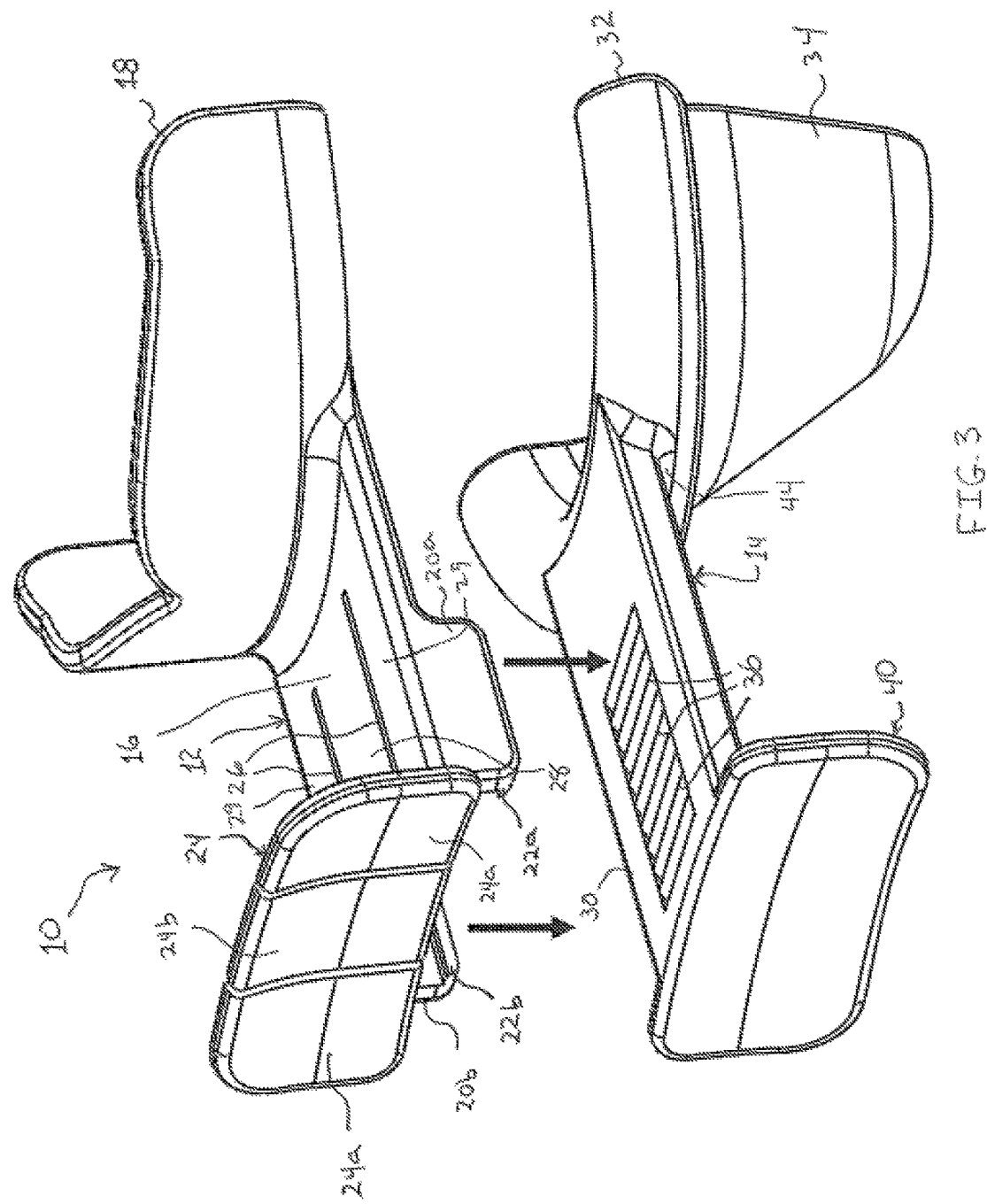

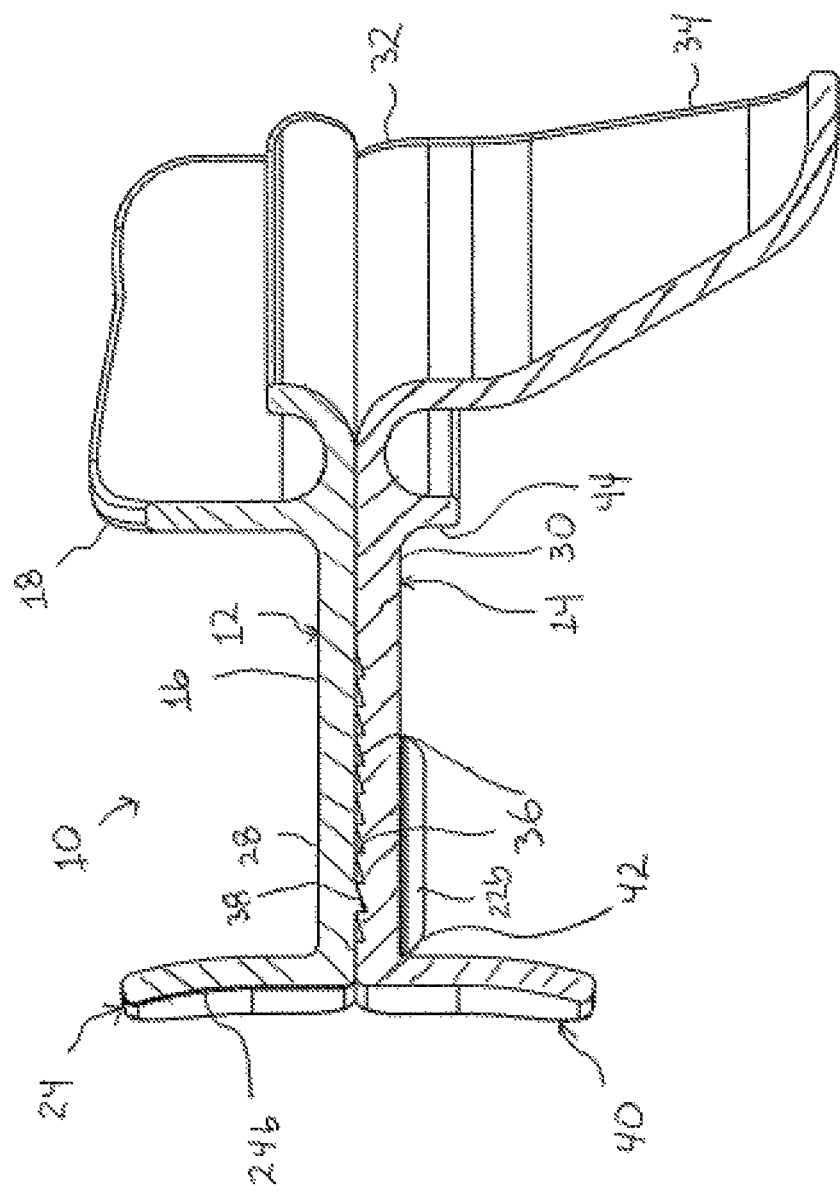

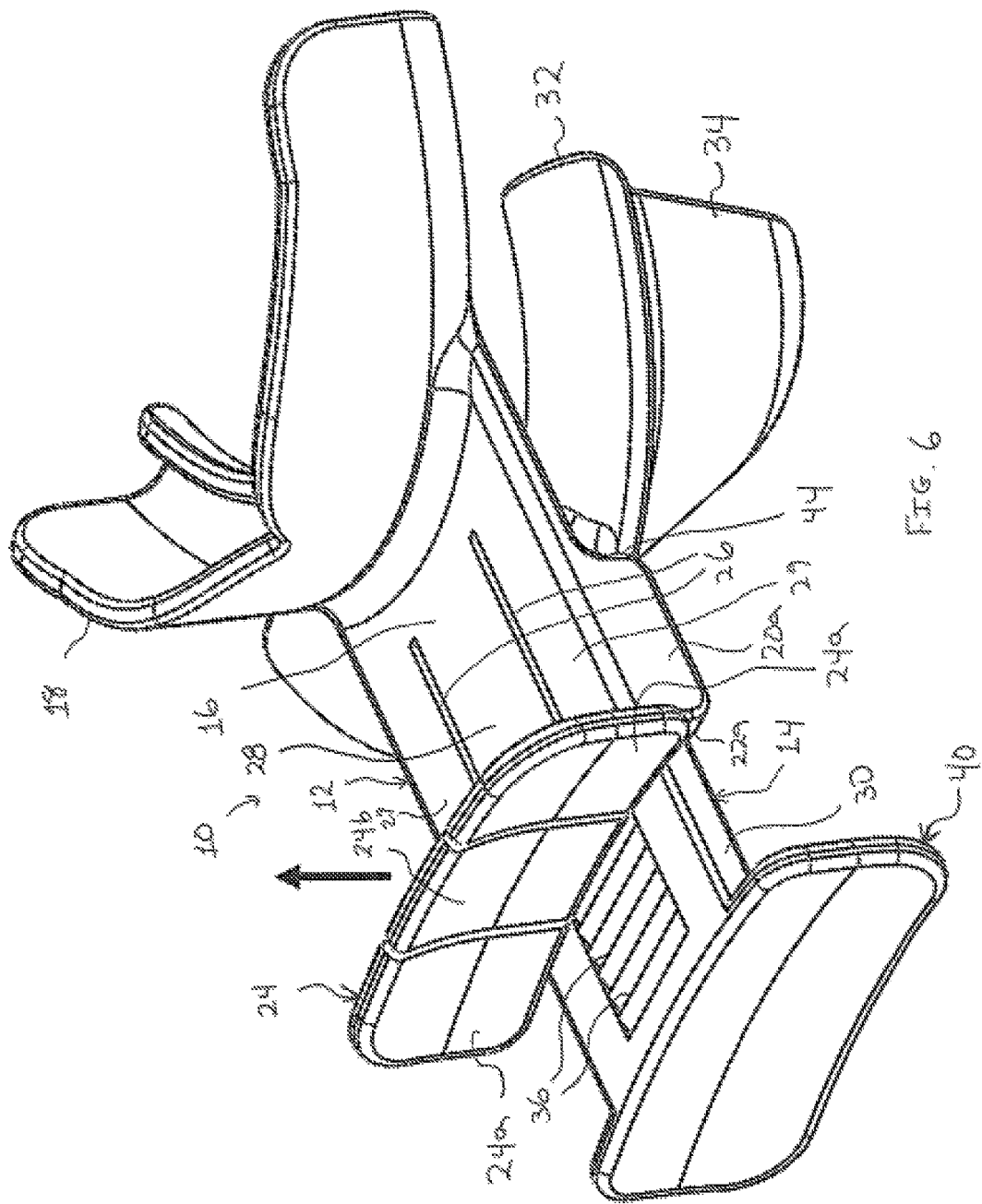

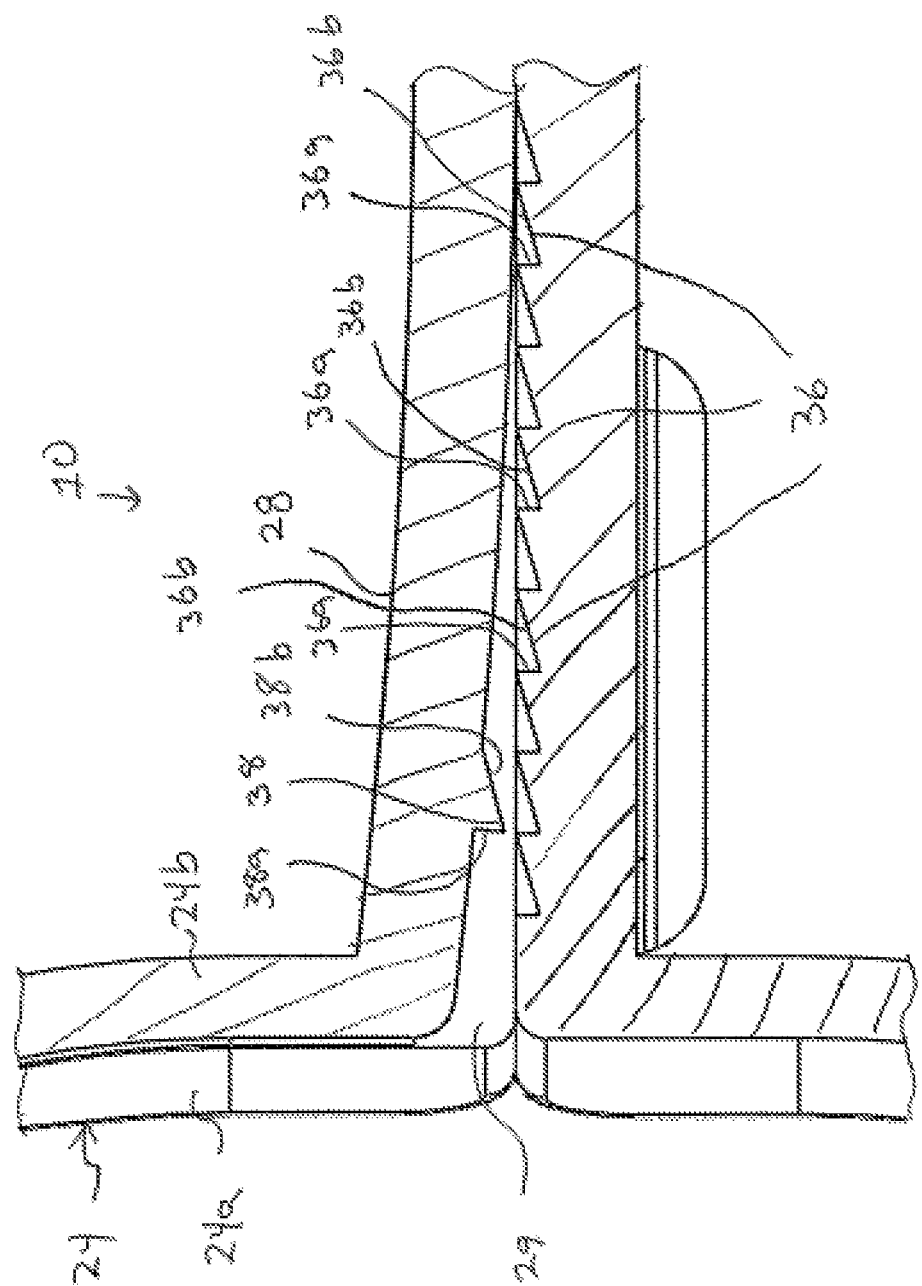

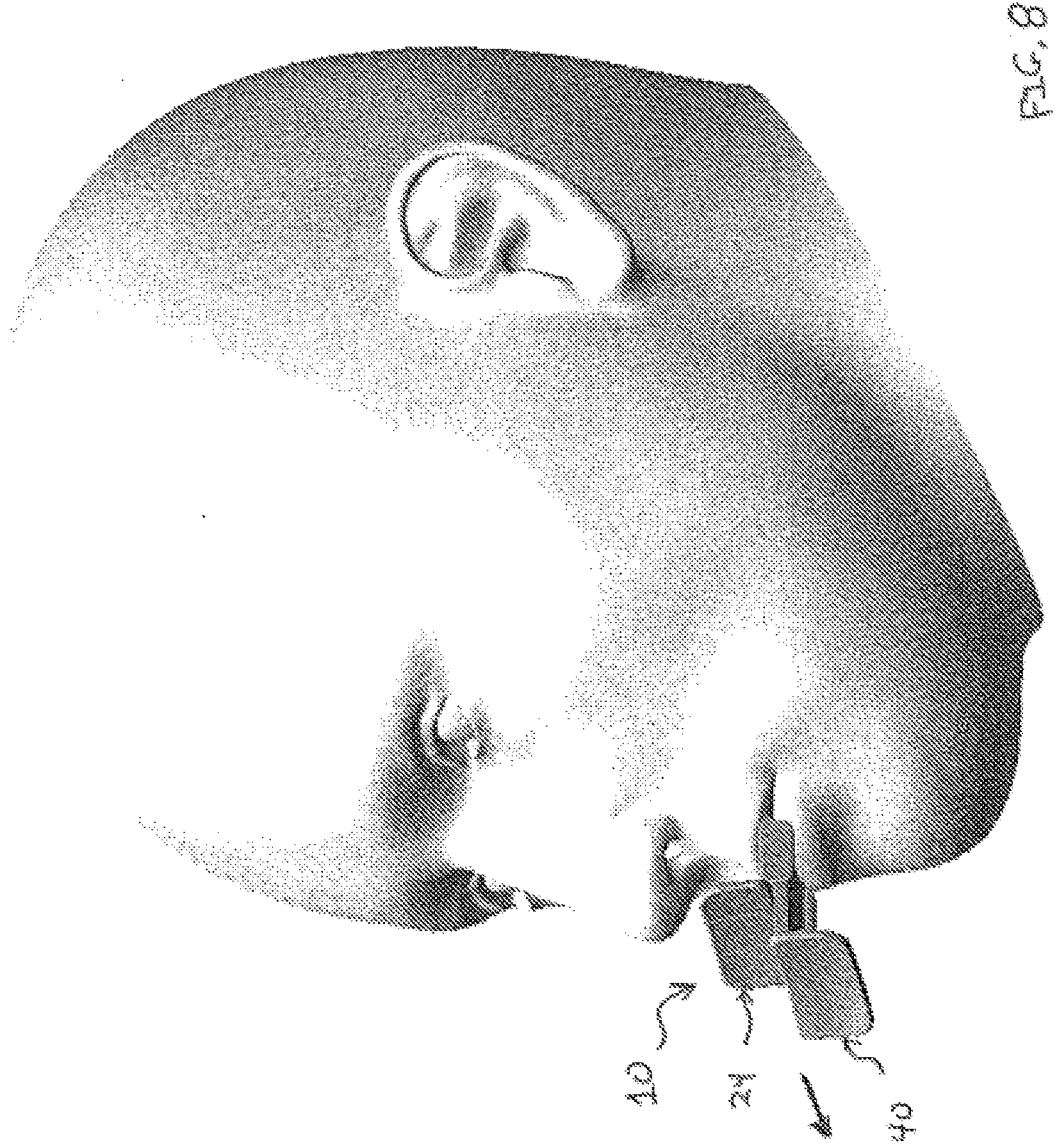

MANDIBULAR SUBLUXATION DEVICE AND METHOD

This is a non-provisional patent application which claims the benefit of U.S. Provisional Patent Application Ser. No. 62/163,007 filed May 18, 2015, the disclosure of which is incorporated herein by reference in its entirety.

FIELD OF THE INVENTION

The present invention relates generally to a mandibular subluxation device and method.

BACKGROUND OF THE INVENTION

Surgical access to zone 3 of the neck can be restrictive due to the triangular bony confines of the vertical mandibular ramus and the mastoid process. Critical anatomic structures residing in the area, namely the internal carotid artery and major cranial nerves, require proper exposure to facilitate structural preservation and procedural implementation. Proper exposure can be challenging particularly in the presences of a short neck, morbid obesity, a high carotid bifurcation or the need for extended carotid dissection above $C_2$. Mandibular subluxation can provide access to these anatomical structures for performing medical procedures.

SUMMARY OF THE INVENTION

According to an embodiment, there is provided a mandibular subluxation device (MSD). The MSD comprises a first mandibular subluxation component including an upper plate and an upper tooth guide. The MSD further comprises a second mandibular subluxation component including a lower plate and a lower tooth guide connected to the lower plate. The first mandibular subluxation component is connected with the second mandibular subluxation component to allow relative longitudinal movement between the first and second mandibular subluxation components between a neutral position and at least one extended position. A ratchet mechanism acts between the first and second mandibular subluxation components. The ratchet assembly allows for movement of the second mandibular subluxation component from the neutral position to an extended position and inhibits movement of the second mandibular subluxation component from an extended position toward the neutral position.

According to an embodiment, there is provided a method of mandibular subluxation. The method comprises positioning an upper tooth guide of a first mandibular subluxation component relative to a patient and positioning a lower tooth guide of a second mandibular subluxation component relative to a patient. The second mandibular subluxation component is in a neutral position when positioned. A force is applied to the second mandibular subluxation component in a direction away from the patient to move the second mandibular subluxation component relative to the first mandibular subluxation component from the neutral position to an extended position thereby to distract the patient's mandible. The second mandibular subluxation component is held in an extended position by a ratchet mechanism on the first mandibular subluxation component and the second mandibular subluxation component.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 3 is an exploded view the embodiment of FIG. 1;

FIG. 5 is a cross-sectional view of the embodiment of FIG. 1;

FIG. 6 is a perspective view of the embodiment of FIG. 1 in an extended position;

FIG. 7 is a cross-sectional view, partially broken away, showing the ratchet mechanism disengaged; and FIG. 8 is a perspective view of the embodiment of FIG. 1 as used.

DETAILED DESCRIPTION OF THE PREFERRED EMBODIMENTS

Figure 1:
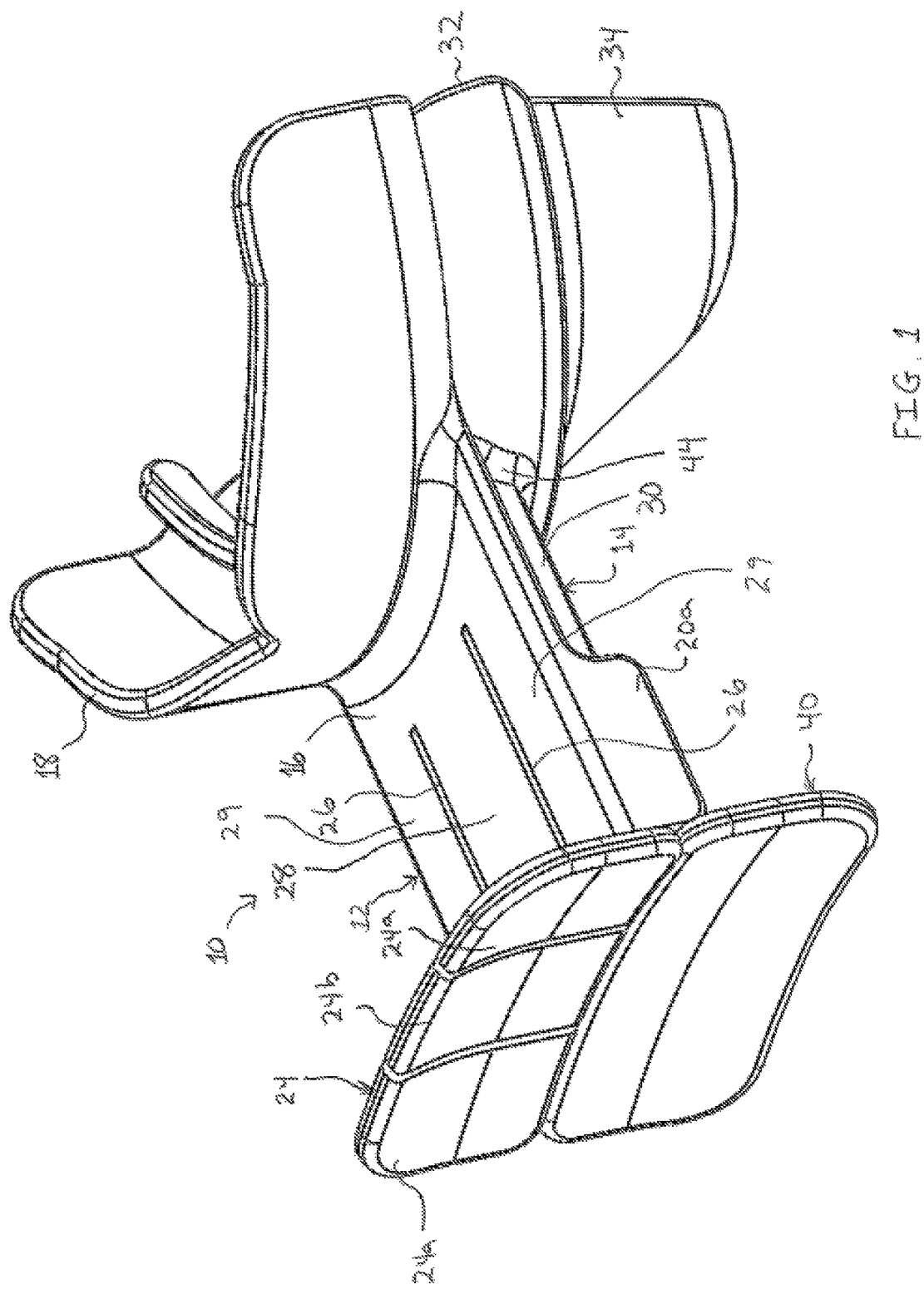
FIG. 1 is a perspective view of an embodiment.

The following description of the preferred embodiment(s) is merely exemplary in nature and is in no way intended to limit the invention, its application, or its uses.

An embodiment of a mandibular subluxation device (MSD) is generally shown at 10. The MSD 10 may be useful to allow for anterior displacement of the vertical ramus of the mandible to provide access to the internal carotid artery and major cranial nerves. As best shown in FIG. 3, the MSD 10 may comprise a first or upper MSD component generally indicated at 12 and a second or lower MSD component, generally indicated at 14. The upper MSD component 12 may comprise an injection molded component. The lower MSD 14 component may comprise an injection molded component. The upper MSD component 12 and lower MSD component 14 may comprise any suitable material.

In the embodiment shown, the upper MSD component 12 has an upper plate 16. The upper plate 16 is preferably connected to an upper tooth guide 18. The upper tooth guide 18 preferably envelopes a dentate or edentulous alveolar ridge of the patient. All or part of the upper tooth guide 18 may be covered with a relatively soft material. By way of non-limiting example, the upper tooth guide 18 may be overmolded with a relatively soft urethane material.

As shown, the upper plate 16 extends from the upper tooth guide 18. The upper plate 16 is preferably generally rectangular. While the upper plate 16 is described as being generally rectangular, it will be appreciated that the upper plate 16 may take any suitable geometrical configuration. As best seen in FIG. 3, the upper plate 16 preferably includes a pair of legs 20a, 20b depending therefrom. The legs 20a, 20b depend from opposite sides of the upper plate 16. Each leg 20a, 20b has a lip 22a, 22b extending therefrom respectively. Each lip 22a and 22b extends in a direction inwardly or toward the direction of the centerline of the upper plate 16. The upper surfaces of each lip 22a and 22b are preferably generally rectangular and are preferably relatively smooth and parallel with the bottom surface of the upper plate 16. The bottom surfaces of each lip 22a and 22b may be angled or ramped. The bottom side of the upper plate 16, legs 20a, 20b and lips 22a and 22b preferably cooperate to form a guide to receive a lower plate 30, as will be described in more detail below.

The upper plate 16 preferably includes a pair of spaced apart slits 26. A center portion 28 of the upper plate 16 is thereby formed between the slits 26. Outer portions 29 of the upper plate are adjacent the slits 26. The legs 20a, 20b depend from the respective outer portions 29. The center portion 28 may flex relative to the outer portion 29 of the upper plate 16 in the vertical direction as the MSD 10 is best shown in FIG. 7.

As best seen in FIGS. 5 and 7, the center portion 28 of the upper plate 16 further includes a pawl 34 extending from the bottom surface thereof. The pawl 38 is part of a ratchet mechanism that is used to maintain the MSD 10 in an appropriate extended position, as will be described in more detail below.

The upper MSD component 12 further includes an upper force receiving plate generally indicated at 24. In the embodiment shown, the upper force receiving plate 24 extends transversely and preferably perpendicularly to the upper plate 16 and is connected thereto. As shown, the upper force receiving plate 24 extends upwardly from the upper plate 16. The upper force receiving plate 24 may be generally curved as shown in the Figures. It will be appreciated, however, that the upper force receiving plate 24 may take any suitable geometric configuration. In certain embodiments, the upper force receiving plate 24 may even constitute the end of the upper plate 16. It will further be appreciated that the upper force receiving plate 24 may be disposed at locations on the upper plate 16 other than at the end thereof.

Figure 2:
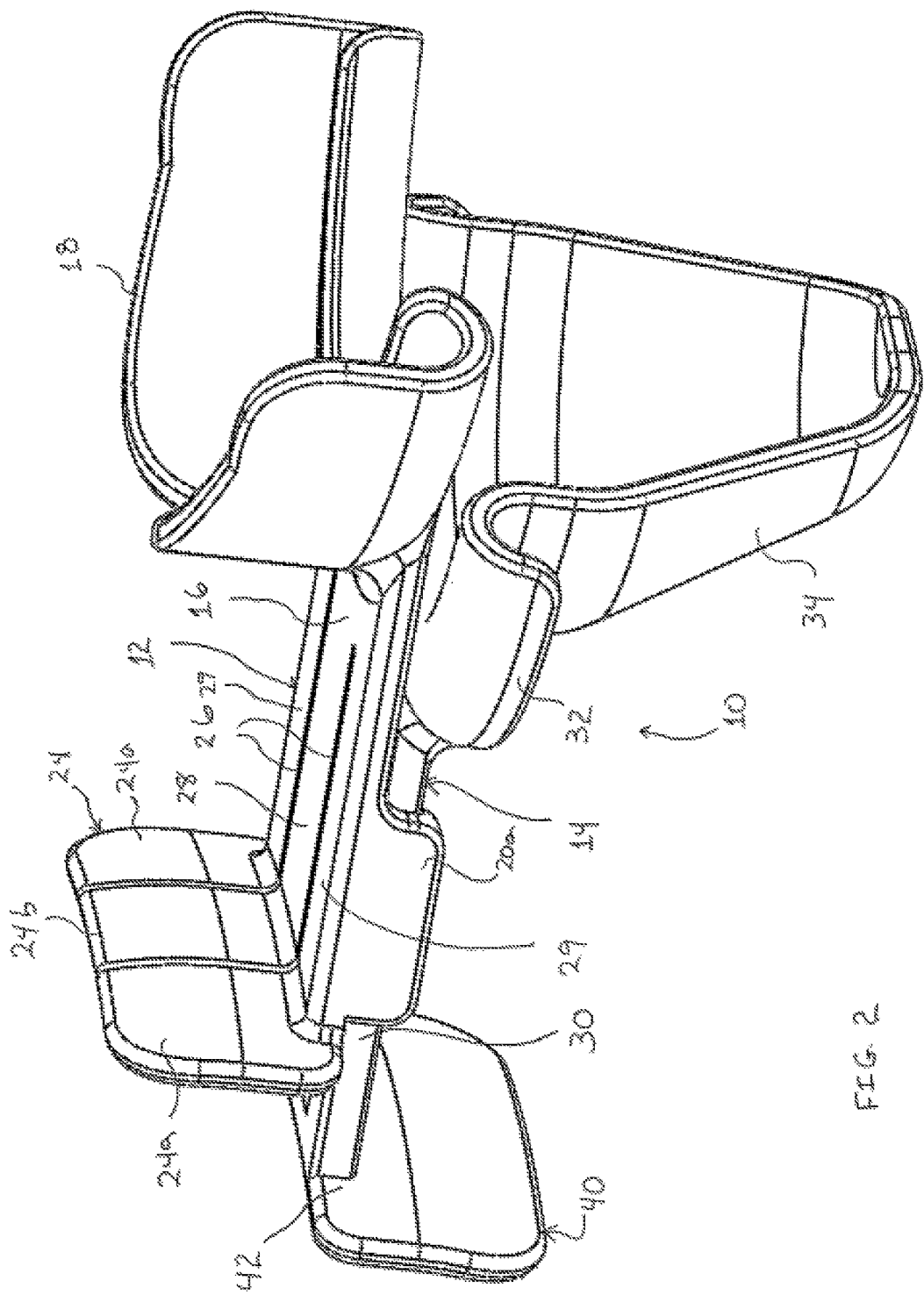
FIG. 2 is a perspective view the embodiment of FIG. 1.

The upper force receiving plate 24 is preferably divided into a plurality of sections; two outermost sections 24a and a center section 24b. As shown in FIG. 2, the slits 26 are preferably contiguous from the upper plate 16 and onto the upper force receiving plate 24. Each of the sections 24a is preferably secured to the outer portions 29 of the upper plate 16. The center section 24b is preferably secured to the center portion 28 of the upper plate 16. In one embodiment as shown, the outermost sections 24a and center section 24b are integrally formed with the outer portions 29 and center portion 28, respectively of the upper plate 16. The center section 24b can flex in the vertical direction, as is best shown in FIG. 7, relative to the outermost sections 24a and along with the center portion 28 of the upper plate 16.

The upper MSD component 12 is preferably molded as a single piece. And as set forth above a relatively softer urethane material may be molded over, or otherwise placed over, the upper tooth guide 18. The upper MSD component 12 is preferably rigid. It will be appreciated, however that the legs 20a, 20b may flex slightly relative to the upper plate 16 when MSD is being assembled, and the center portion 28 and center section 24b can flex relative to the outer portions 29 of the upper plate 16 and the outermost sections 24a of the upper force receiving plate 24, respectively.

In the embodiment shown, the lower MSD component 14 has a lower plate 30. The lower plate 30 is preferably connected to a lower tooth guide 32. The lower tooth guide 32 further may include a lower dental guard 34 that extends such that it may engage the lingual aspect of the mandible of a patient. All or part of the lower tooth guide 32 and dental guard 34 may be covered with a relatively soft material. By way of non-limiting example, the lower tooth guide 32 and/or the lower dental guard 34 may be overmolded with a relatively soft urethane material.

As best seen in FIG. 3, the lower plate 30 extends from the lower tooth guide 32. The lower plate 30 is preferably generally rectangular. While the lower plate 30 is described as being generally rectangular, it will be appreciated that the lower plate 30 may take any suitable geometrical configuration. The lower plate 30 has a plurality of teeth 36. The teeth 36 are preferably located in a position below the top surface of the lower plate 30. It will be appreciated, however, that the teeth 36 may extend above the top surface of the lower plate 30. The teeth 36 of the lower plate 30 cooperate with the pawl 38 on the upper plate 16 to form a ratchet mechanism. The teeth 36 and pawl 38 cooperate to allow the lower plate 30 to move outwardly, from the perspective of the patient, relative to the upper plate 16 from a neutral position to an extended position and to become secured in any number of extended positions. More specifically each tooth 36 has a generally vertical surface 36a and a ramped or angled surface 36b. Similarly, the pawl 38 includes a generally vertical surface 38a and a ramped or angled surface 38b. The generally vertical surface 38a of the pawl 38 can engage the generally vertical surface 36a of a tooth 36 to inhibit longitudinal movement of the lower plate 30 in one direction. The ramped surface 36b of the teeth 36 allows longitudinal movement of the lower plate 30 in one direction by engaging the ramped surface 38b and guiding the pawl 38 over the respective tooth 36. More specifically, as the lower plate 30 is moved outwardly, away from the patient, the ramped surface 36b of each tooth 36 engages the ramped surface 38b of the pawl 38 to thereby guide the pawl 38 over the respective tooth 36. This allows the lower plate 30 to be moved in the outward longitudinal direction relative to the patient. Once the pawl 38 passes over the tooth 36, the pawl 38 descends and the vertical surface 38a of the pawl 38 can engage the vertical surface 36a of the tooth to inhibit movement of the lower plate 30 in the longitudinal direction toward the patient. That is, the pawl 38 is biased in such a way to cause the pawl 38 to descend into engagement with the plurality of teeth 36. In this way, a clinician can move the lower plate 30 to the desired extended position relative to the upper plate 16 and the ratchet mechanism will maintain the lower plate 30 in the desired extended position. It will be appreciated that any number of teeth 36 may be used and may be placed to allow any number of desired extended positions.

The lower MSD component 14 further includes a lower force receiving plate generally indicated at 40. In the embodiment shown, the lower force receiving plate 40 extends transversely to the lower plate 30 and is connected thereto. As shown, the lower force receiving plate 40 extends downwardly from the lower plate 30. The lower force receiving plate 40 may be generally curved as shown in the Figures. It will be appreciated, however, that the lower force receiving plate 40 may take any suitable geometric configuration. It will be appreciated that the lower force receiving plate 40 may be disposed at locations on the lower plate 30 other than at the end thereof.

Figure 4B:
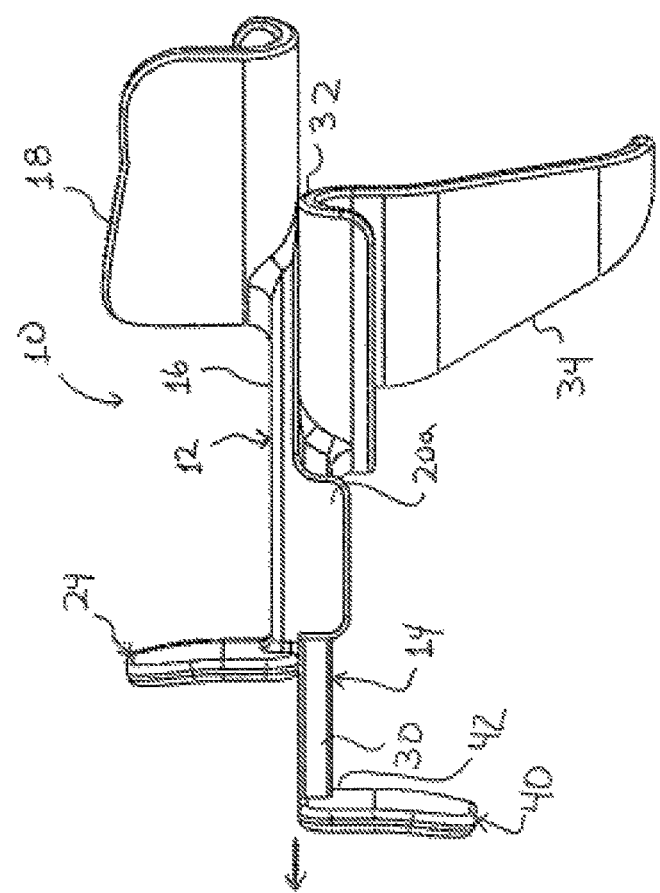
FIG. 4b is a side view the embodiment of FIG. 1 in an extended position.
Figure 4A:
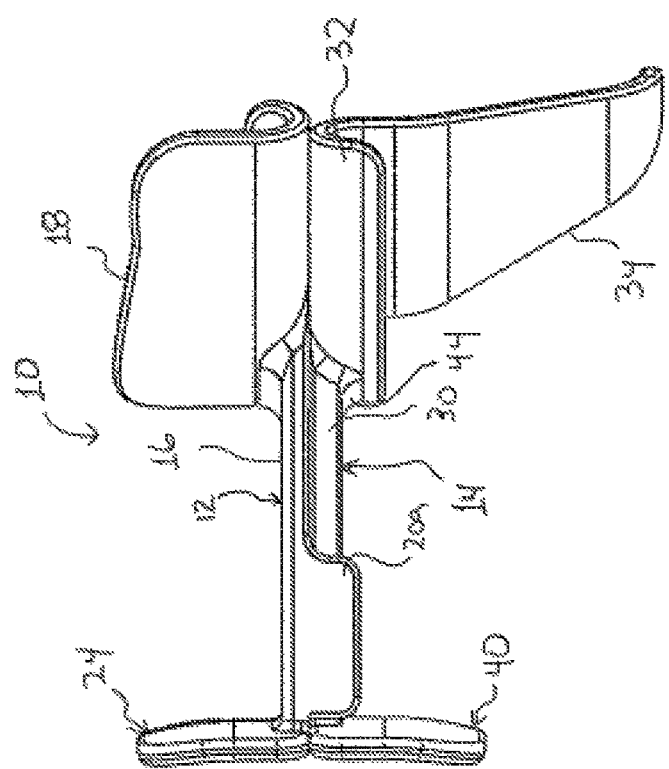
FIG. 4a is a side view the embodiment of FIG. 1 in a neutral position.

The back side of the lower force receiving plate 40 may include an area or surface 42 that acts as a hard stop as the lower MSD component 14 is moved from an extended position to the neutral position. As shown in FIGS. 4a and 4b, the surface 42 may engage a portion of the leg 20a and leg 20b, not shown, to inhibit further movement of the lower MSD component 14 in a direction toward the patient. Such a hard stop may prevent the lower MSD component 14 from moving past the neutral position.

The lower tooth guide 32 may include an area or surface 44 that acts as a hard stop as the lower MSD component 14 is moved to a fully extended position. As shown in FIG. 4b, the surface 44 may engage a portion of the leg 20a and leg 20b, not shown, to inhibit further movement of the lower MSD component 14 in the direction away from the patient. Such a hard stop may prevent the lower MSD component 14 from moving outwardly to a fully extended position past a predetermined amount. This may reduce the ability of the lower MSD component 14 from move too far and causing dislocation at the joint. In one preferred embodiment, the length of travel allowed between the hard stops may be about 15 mm.

The lower MSD component 14 is preferably molded as a single piece. And as set forth above a relatively softer urethane material may be molded over, or otherwise placed over, the lower tooth guide 18. The lower MSD component 14 is preferably rigid.

As set forth above, the bottom side of the upper plate 16, legs 20a, 20b and lips 22a and 22b preferably cooperate to form a guide to receive a lower plate 30. More specifically, when the MSD 10 is assembled, the lower plate 30 is received in the space between the bottom side of the upper plate 16, the legs 20a and 20b and the lips 22a and 22b. When the MSD is assembled, the lower plate 30 is moveable in the longitudinal direction relative to the upper plate 16 within the guide or space formed between the bottom side of the upper plate 16, legs 20a, 20b and lips 22a and 22b.

To assemble the MSD 10, the upper MSD component 12 is positioned over the lower MSD component 14 as shown in FIG. 3. The upper plate 16 may be aligned over the lower plate 30. The upper plate 16 and lower plate 30 are moved toward each other as indicated by the arrows in FIG. 3. The lower plate 30 may contact the ramped surfaces of the lips 22a and 22b on the legs 20a and 20b, respectively. As the upper plate 16 and lower plate 30 continue to move toward each other, the legs 20a and 20b flex outwardly relative to the axial direction of the upper plate 16. This allows the upper plate 16 to be positioned adjacent to the lower plate 30. Once the lower plate 30 has moved past the lips 22a, 22b, the legs 20a, 20b return to their unflexed position. In this position, the lower plate 30 is retained in the guide or space that is defined by the bottom side of the upper plate 16, legs 20a, 20b and lips 22a and 22b. The pawl 34 may engage one of the teeth 32 in the lower plate 30. It is preferred that when the MSD 10 is assembled, the upper tooth guide 18 and lower tooth guard 32 are positioned adjacent each other as best seen in FIG. 4a. This may be referred to as the neutral or non-extended position.

In order to use the MSD 10, the assembled MSD 10, in the neutral position, is positioned relative to a patient. The upper tooth guide 18 is positioned to envelope a dentate or edentulous alveolar ridge of the patient. The lower tooth guide 32 is positioned in such a way the dental guard 34 extends to the lingual aspect of the patient's mandible. By using an upper tooth guide 18 and a lower tooth guide 32 as set forth, the MSD 10 can be used with a dentate or non-dentate application with a variety of dental arch shapes. It will be appreciated that in some instances it may be necessary to place the MSD 10 in an extended position prior to positioning the MSD 10 relative to the patient. Once the MSD 10 is positioned relative to the patient, the patient's mandible can be distracted as follows. A clinician, such as a surgeon, can place his thumbs on the distal surfaces of outermost sections 24a (those furthest away from the patient) of the upper force receiving plate 24. The clinician can place his index or other fingers on the back side (closest to the patient) of the lower force receiving plate 40. The clinician can hold his thumbs in the same position relative to the patient in such a way that the upper MSD component 12 remains in a relatively fixed position relative to the patient. The clinician can apply a force to the lower force receiving plate in a direction away from the patient, as shown by the arrows in FIGS. 4b and 8. By applying such a force, the lower MSD component 14 moves longitudinally and away from generally perpendicular to the patient to an extended position, as best seen in FIGS. 4b and 8. The ratchet mechanism, pawl 38 and teeth 36, allow movement of the lower MSD component 14 in one direction, outwardly away from the patient, while inhibiting movement in the opposite direction. Because there are several teeth 36, the clinician can extend lower MSD component to any desired extended position along the subluxation path relative to the upper MSD component 12. This allows for relatively smooth mandibular distraction while minimizing any torque. This anterior mandibular distraction causes anterior displacement of the vertical ramus of the mandible which may result in subluxation of the mandibular joint. This, in turn, may allow for, inter alia, greater exposure to the carotid artery, major cranial nerves, or parapharyngeal space in order to perform procedures.

The length of travel of the lower MSD component 14 relative to the upper MSD component is limited by the hard stop, the surface 44 on the lower MSD component engaging the legs 20a, 20b of the upper MSD component 12. By providing a hard stop, the length of travel of the lower MSD component 14 relative to the upper MSD component can be controlled. This may help inhibit dislocation of the mandibular joint. In one embodiment, the lower MSD component 14 may extend up to about 15 mm before the hard stop occurs when the surface 44 engages the legs 20a, 20b to inhibit further extension of the lower MSD component 14 relative to the upper MSD component 12.

Once the clinician is done with the procedure, the MSD 10 can be returned to the neutral position. This may be done by the clinician applying an upward force to the center section 24b of the upper force receiving plate 24. As best seen in FIG. 7, the center section 24b can be raised sufficiently to raise the center section 28 of the upper plate 16 to disengage the pawl 38 from the teeth 36 of the lower plate 30. Once the pawl 38 is disengaged from the teeth 36, the lower MSD component 14 can return to the neutral position. A hard stop, surface 42, on the lower force receiving plate 40 engaging the legs 20a, 20b of the upper MSD component 12, inhibits movement of the lower MSD component 14 past the neutral position. Upon returning the MSD 10 to the neutral position, the clinician may then remove the MSD 10 from the patient.

The design of the MSD 10 may provide for a single use device which is relatively easy to use. The design also may avoid the need to require dental mold impressions for each patient. Also, the design of the MSD may provide an MSD that is atraumatic to the nasal cavity or the oral cavity.

The embodiment has been described in an illustrative manner. It is to be understood that the terminology which has been used is intended to be in the nature of words of description, rather than of limitation. Obviously many modifications and variations are possible in light of the above teachings. It is therefore to be understood that the scope of the invention is set forth in the claims.

What is claimed is:
1. A mandibular subluxation device comprising:
a first mandibular subluxation component including an upper plate and an upper tooth guide connected to the upper plate;

a second mandibular subluxation component including a lower plate and a lower tooth guide connected to the lower plate;

the first mandibular subluxation component connected with the second mandibular subluxation component to allow relative longitudinal movement between the first and second mandibular subluxation components between a neutral position and at least one extended position; and a ratchet mechanism acting between the first and second mandibular subluxation components, the ratchet mechanism allowing for movement of the second mandibular subluxation component from the neutral position to an extended position and inhibiting movement of the second mandibular subluxation component from an extended position toward the neutral position.

2. The mandibular subluxation device as set forth in claim 1 wherein the ratchet mechanism comprises a pawl on one of the upper plate or the lower plate and a plurality of teeth on the other of the upper plate or the lower plate.

3. The mandibular subluxation device as set forth in claim 2 wherein the upper plate further comprises a pair of spaced apart slits, the upper plate including a central portion between the spaced apart slits and outer portions disposed outwardly of the slits.

4. The mandibular subluxation device as set forth in claim 3 wherein the central portion of the upper plate can flex relative to the outer portions, the central portion including the pawl thereon.

5. The mandibular subluxation device as set forth in claim 4 wherein the first mandibular subluxation component further comprises an upper force receiving plate extending transversely to the upper plate having a pair of outermost sections secured to the outer portions of the upper plate and a center section secured to the center portion of the upper plate.

6. The mandibular subluxation device as set forth in claim 4 wherein the plurality of teeth are disposed on the lower plate and wherein the pawl is adapted to engage at least one tooth.

7. The mandibular subluxation device as set forth in claim 6 wherein the second mandibular subluxation component further comprises an lower force receiving plate extending transversely to the lower plate.

8. The mandibular subluxation device as set forth in claim 6 wherein the pawl includes a ramped surface and a generally vertical surface and each tooth includes a ramped surface and a generally vertical surface, the ramped surfaces of the pawl and tooth allow the pawl to move over the tooth as the second mandibular subluxation component is being moved to an extended position and the generally vertical surfaces of the pawl and tooth cooperating to inhibit movement of the second mandibular subluxation component from being moved from an extended position toward the neutral position.

9. The mandibular subluxation device as set forth in claim 8 wherein the first mandibular subluxation component includes a pair of legs depending from the outer portions of the upper plate, each of the legs including a lip thereon, the upper plate, legs and lips cooperating to form a guide to receive the lower plate of the second mandibular subluxation component.

10. The mandibular subluxation device as set forth in claim 8 wherein the central portion of the upper plate is adapted to receive a force to move the center section so as to disengage the pawl from the tooth to allow the second mandibular subluxation component to move toward the neutral position.

11. The mandibular subluxation device as set forth in claim 10 wherein the second mandibular subluxation component includes at least one stop for limiting relative longitudinal movement between the first mandibular subluxation component and the second mandibular subluxation component.

12. A method of mandibular subluxation comprising:
    positioning an upper tooth guide of a first mandibular subluxation component relative to a patient and positioning a lower tooth guide of a second mandibular subluxation component relative to a patient, the second mandibular subluxation component being in a neutral position;
    applying a force to the second mandibular subluxation component in a direction away from the patient to move the second mandibular subluxation component relative to the first mandibular subluxation component from the neutral position to an extended position to thereby distract the patient mandible; and
    maintaining the second mandibular subluxation component in an extended position by a ratchet mechanism on the first mandibular subluxation component and the second mandibular subluxation component.

13. The method of mandibular subluxation as set forth in claim 12 further comprising releasing the ratchet mechanism to thereby allow the second mandibular subluxation component to be moved toward the neutral position.

* * * * *